United States Patent [19]

Barrett

[11] Patent Number: 4,664,666
[45] Date of Patent: May 12, 1987

[54] INTRAOCULAR LENS IMPLANTS

[75] Inventor: Graham D. Barrett, City Beach, Australia

[73] Assignee: Ezekiel Nominees Pty. Ltd., Australia

[21] Appl. No.: 640,098

[22] Filed: Aug. 13, 1984

[30] Foreign Application Priority Data

Aug. 30, 1983 [AU] Australia .............................. PG1120

[51] Int. Cl.⁴ .............................................. A61F 2/14
[52] U.S. Cl. ...................................................... 623/6
[58] Field of Search .................................. 3/13; 623/6

[56] References Cited

U.S. PATENT DOCUMENTS

| 3,961,379 | 6/1976 | Highgate | 623/6 X |
| 4,113,088 | 9/1978 | Binkhorst | 3/13 X |
| 4,242,762 | 1/1981 | Tennant | 623/6 |
| 4,249,272 | 2/1981 | Poler | 623/6 |
| 4,254,509 | 3/1981 | Tennant | 623/6 |
| 4,257,521 | 3/1981 | Poler | 206/51 |
| 4,261,065 | 4/1981 | Tennant | 3/13 |
| 4,315,336 | 2/1982 | Poler | 3/13 |
| 4,402,579 | 9/1983 | Poler | 3/13 X |
| 4,423,809 | 1/1984 | Mazzocco | 3/13 X |
| 4,424,597 | 1/1984 | Schlegel | 3/13 |
| 4,449,257 | 5/1984 | Koeniger | 3/13 |
| 4,556,998 | 12/1985 | Siepser | 623/6 |
| 4,573,998 | 3/1986 | Mazzocco | 623/6 |

FOREIGN PATENT DOCUMENTS

| 2114315 | 8/1983 | United Kingdom | 3/13 |
| 2151371A | 7/1985 | United Kingdom | 623/6 |

OTHER PUBLICATIONS

Lens Styles from Cilco (Brochure Advertisement-6 pp.) Cilco, Inc., 1616 13th Ave., Box 1680, Huntington, West Va 25717, pp. 1, 4 and 6 cited, Oct. 1982 (note Lenses on p. 4 & 6).

"The New Soft Intraocular Lens Implant" by K. R. Mehta et al., Am Intra-Ocular Implant Soc. J., vol. IV, Oct. 1978, pp. 200-205.

"The Soft Intraocular Implant", by K. R. Mehta et al., The Cornea in Health & Disease (VIth Congress of the European Society of Ophthalmology); Royal Society of Medicine International Congress & Symposium Series No. 40, pp. 859-863, 1981.

M. F. Refojo, "Ophthalmic Hydrogels", *Technomic*, Technomic Publishing Company, Inc. (1980), p. 171-185.

Wichterle et al., "Ofthalmol.", vol. 16, pp. 154-159 (1960).

Epstein, British Journal of Ophthalmology, vol. 41, pp. 368-376 (1957).

Epstein, British Journal of Ophthalmology, vol. 43, pp. 29-33 (1959).

Edward Epstein, American Intraocular Implant Society Journal, vol. 7, No. 1, pp. 66-67, (1981).

Mazzocco et al., Soft Implant Lens In Cataract Surgery, Chapter 11, pp. 143-150, 1986, (Chapter 11 by Epstein).

Kwitco, Psuedophakia, Current Trends and Concepts, Chapter 1, pp. 3-30 (1980).

*Primary Examiner*—Ronald L. Frinks
*Attorney, Agent, or Firm*—Lowe, Price, Leblanc, Becker & Shur

[57] ABSTRACT

An intraocular lens suitable for implantation in the human eye to replace the natural crystalline lens comprising a self-supporting lens formed entirely of a hydrogel and having a relatively thick optical portion with relatively thin resilient flange means extending away from the optical portion, the flange means being arranged to retain the implant in place in the eye.

17 Claims, 14 Drawing Figures

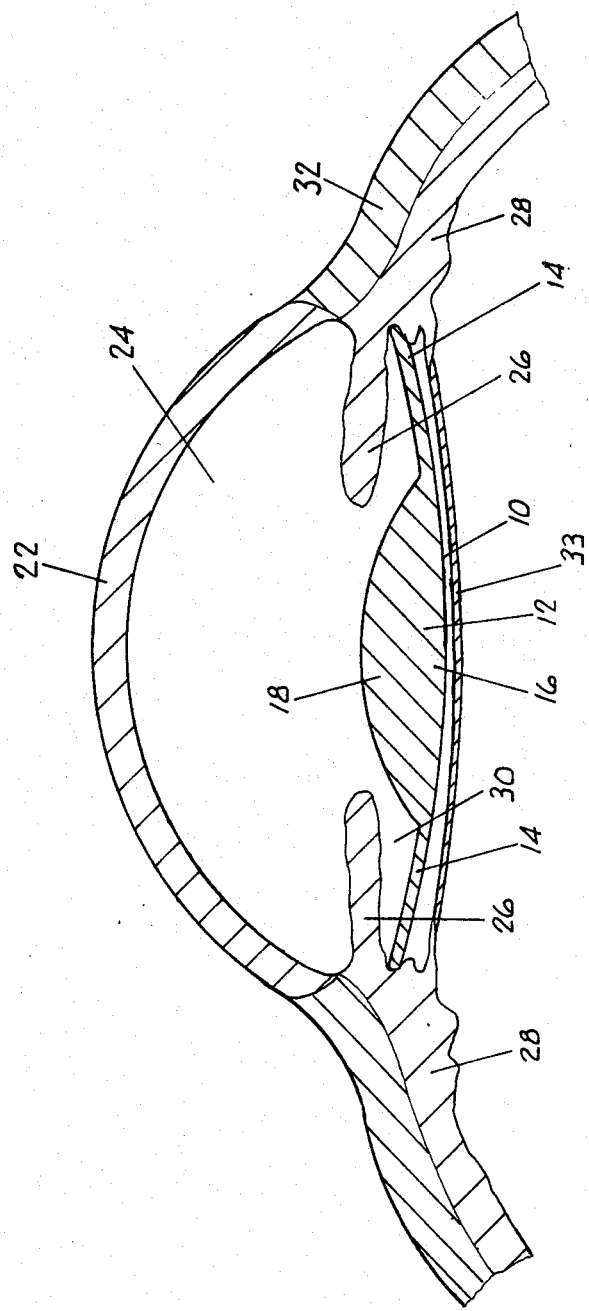

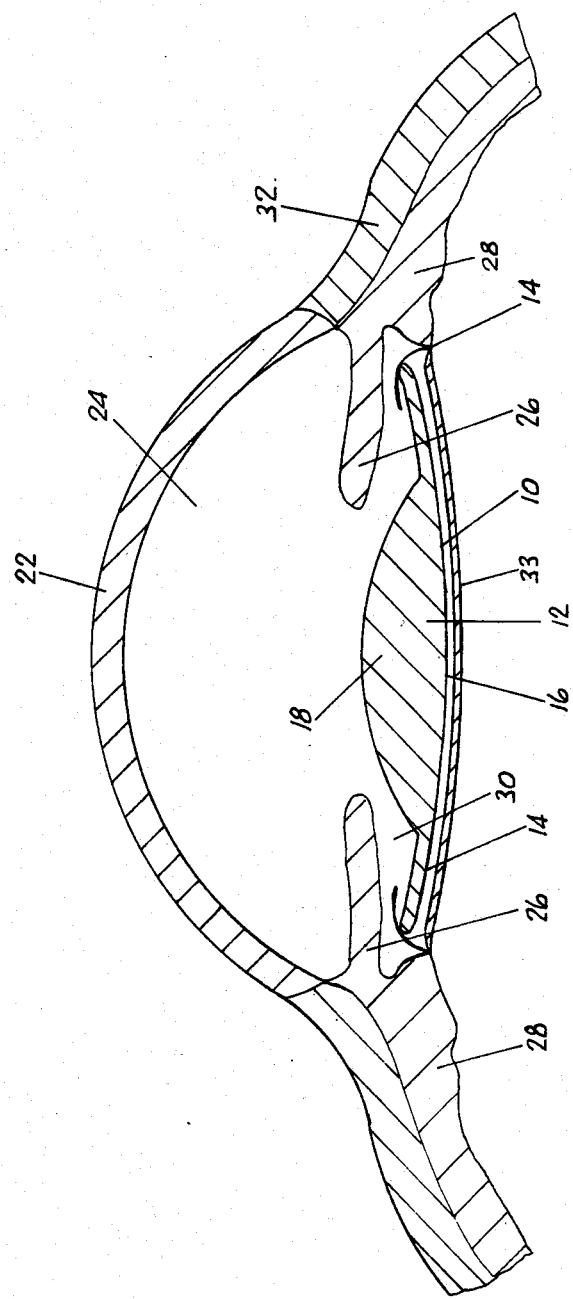

INTRAOCULAR LENS IMPLANTS

The present invention relates to intraocular lens. It is known to replace the natural crystalline lens following cataract extraction. Many people on whom cataract operations are performed receive an intraocular lens implant. However, there is a need for a safer and more effective intraocular lens than those which have been available hitherto. The most commonly used material for intraocular lens has been polymethylmethacrylate (PMMA). PMMA has a number of characteristics making it suitable for use as an intraocular lens implant. However, it has been shown to be particularly injurious to the corneal endothelium. The corneal endothelium is a thin layer at the back of the cornea. The maintenance of corneal clarity is dependent on the endothelium which is essentially non-regenerative. There appears to be a bio-physical interaction between the hydrophobic PMMA and the endothelium such that even momentary touch on insertion will cause significant endothelial cell disruption by adherence of the cells to the lens surface.

Loss of endothelial cells at the time of surgery can lead to loss of corneal transparency several years later. There are other problems attendant with the use of PMMA as an implant material.

In accordance with the present invention there is provided a self-supporting intraocular lens formed of a hydrogel.

A hydrogel is an organic polymeric or copolymeric material comprising hydrophilic monomers. The hydrogel material swells upon being hydrated and becomes soft and flexible. One particularly useful hydrogel is hydroxyethyl methacrylate (HEMA) and it has been found that this material causes little endothelial damage on contact. Also, since hydrogels are hydrophilic in nature endothelial damage is generally less than with PMMA.

Other types of hydrogel which may be used in the present invention are copolymers of vinyl pyrrolidone with HEMA or methyl methacrylate, copolymers of glyceryl methacrylate and methyl methacrylate and copolymers of HEMA and diacetone acrylamide.

The hydrogel intraocular lens of the present invention could be useful in the anterior chamber of the eye or the posterior chamber, but it is particularly envisaged for use in the posterior chamber.

It has been found in particular that a HEMA hydrogel lens manufactured from HEMA having the capability of absorbing about 38% of its weight of water, makes a particularly useful posterior chamber intraocular lens.

Preferably, the intraocular lens implant is of integral construction and comprises a relatively thick optical portion having relatively thin resilient flange means extending away from it, said flange means being arranged to retain the implant in place in the eye.

The present invention will now be described, by way of example, with reference to the accompanying drawings, in which:

FIG. 4a is a cross-sectional view of an eye with an implant according to FIGS. 1 and 2 in place with a ciliary sulcus placement;

FIG. 4b is a cross-sectional view of an eye with an implant according to FIGS. 1 and 2 in place with a capsule bag placement;

Figure 1:
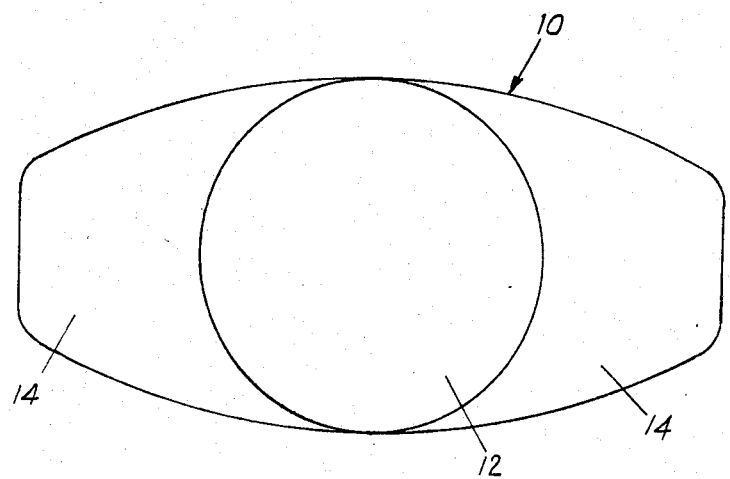
FIG. 1 is a plan view of a self-supporting intraocular lens in accordance with one embodiment of the present invention.
Figure 2:
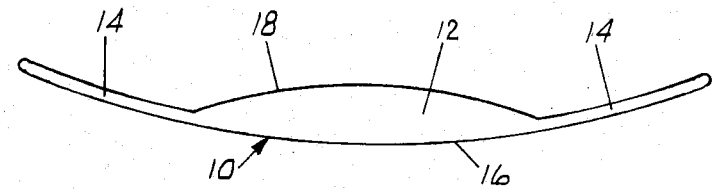
FIG. 2 is a side elevation of the intraocular lens implant of FIG. 1.

In FIGS. 1 and 2, there is shown a self-supporting intraocular lens 10 comprising a central optical portion 12 which is in the form of a lens. As shown, the lens construction does not rely on the iris for support. The central optical portion 12 is flanked by laterally extending flanges 14. The implant has a posterior face 16 and an anterior face 18. The lens implant of FIGS. 1 and 2 is arranged to be inserted in the posterior chamber of an eye.

Figure 3:
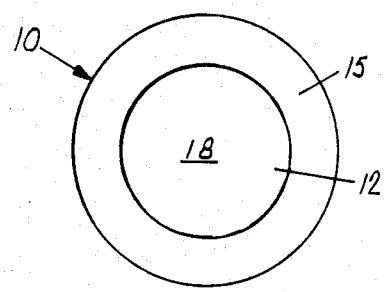
FIG. 3 is a plan view of an intraocular lens implant in accordance with another embodiment of the present invention.

As can be seen in FIG. 2, the optical portion 12 is of asymmetrical biconvex construction which gives good optical resolution. The posterior face 16 is at a standard curvature such as a curve having a radius of about 17 mm. The posterior face 16 is, in this case, a non-variable optical surface whilst the anterior face 18 is an optical surface of varying power. In other lens constructions, the anterior face 18 may be a non-variable optical surface whilst the posterior face 16 may be an optical surface of varying power. Thus, in the embodiment illustrated in FIG. 2, the optical properties of the optical portion 12 can be varied by varying the curvature of the anterior face of the optical portion 12. The ratio of curvature is preferably approximately 3:1 which computer analysis shows to provide optimum ocular resolution for an intraocular lens. The power of each eye is different and therefore the thickness of the optical portion 12 and the curvature of the anterior face 18 thereof will vary from case to case. The technique for forming the correct shape of the anterior face and thickness of the optical portion 12 are known. The lens implant shown in FIG. 3 is similar to that shown in FIGS. 1 and 2, except that the flanges 14 have been replaced by a single circular flange 15 which completely surrounds the optical portion 12. The flange 15 is of similar cross-sectional shape and thickness to the flanges 14. The curvature of the posterior face 16 is preferably such that the resultant lens will be of asymmetrical biconvex construction with the posterior face having the larger curvature as shown in FIG. 2.

Further, the optical portion 12 and flanges 14 are formed in an integral unit, that is the entire implant 10 is formed in one piece. The flanges 14 may be of a wide variety of thickness but are preferably between 0.02 and 0.2 mm thick. More preferably, the flanges 14 are between 0.10 and 0.18 mm thick such as about 0.14 mm thick. The optical portion 12 is thicker than the flanges 14 but, as described above, its actual thickness will vary with optical requirements of the lens implant 10. A typical thickness for the optical portion 12 is about 0.9 mm.

The implant 10 is formed of a hydrogel material such as HEMA and the flanges 14 are therefore resilient. However, the optical portion 12 is thick enough to be sufficiently rigid to provide stable optical correction.

As can be seen in FIG. 2, the flanges 14 have a similar curvature to the posterior face 16. Thus the flanges 14 project forwardly and, as will be described, dispose the implant 10 away from the iris in use.

Further, the flanges 14 may be transversely tapered as can be seen in FIG. 1. This enables the flanges 14 to be inserted even into a small pupil. The flanges 14 may, for example, taper from 6 mm at the optical zone 12 to 2 mm at their outer extremities.

The lens implant 10 can be manufactured by any suitable technique such as by forming a blank on a lathe, polishing the lens implant, checking the thicknesses of the various parts of the lens implant, checking in the dry state for any flaws, cleaning to remove residual wax or polish and then bathing the implant in saline solution. The hydrated implant can then be washed in a Soxhlet system and again examined for defects in the hydrated state. Other suitable manufacturing techniques include moulding or pressing to form a lens implant in accordance with the present invention. The power of the lens is measured in the hydrated state. The lens dimensions are thus measured in the hydrated state. Finally, the lens implant is placed in a sealed vial in a physiologically acceptable electrolyte solution and autoclaved to sterilise it. The electrolyte solution must be a balanced or isotonic salt solution which will hydrate the lens implant 10 and be compatible with the human eye. The vial is preferably a glass vial.

In FIG. 4a there is shown an eye comprising a cornea 22 which has an endothelium layer on its inner face. Behind the cornea there is an anterior chamber 24 which is filled with aqueous fluid. At the rear of the chamber 24 there is located the iris 26 which is in two parts separated by a gap which constitutes the pupil of the eye. At its outer edge the iris 26 is connected to ciliary sulcus 28. The region behind the iris 26 forms a posterior chamber 30 which also contains aqueous fluid. To the front of the ciliary sulcus 28 is the white 32 of the eye. To the rear of the posterior chamber is the posterior capsule 33 of the eye. As can be seen in FIG. 4a the lens implant 10 of FIGS. 1 and 2 is mounted in the eye in the posterior chamber 30. The lens implant 10 is retained in place by engagement of the flanges 14 in the ciliary sulcus 28. There are two preferred methods of fixation for a posterior chamber lens in accordance with the present invention. The first method is illustrated in FIG. 4a in which the lens is fixed in place by engagement with the ciliary sulcus 28 and in this case the lens width may be from about 12 to 14 mm such as about 12.5 mm.

The second method of fixation is illustrated in FIG. 4b and is by means of the capsular bag of the eye. In this case the capsular bag, fixes the lens in place. The lens intended for capsular bag placement would typically have a diameter in the range from about 10 to 12 mm such as about 11 mm. In other respects the lens of FIG. 4b is similar to that of FIG. 4a.

The intraocular lens implant of the present invention can take many forms.

FIGS. 5 to 12 illustrate various modifications of the lens implant shown in FIG. 4 and like reference numerals denote like parts. The lens implants of FIGS. 5,6, 7 and 11 are intended for posterior chamber placement by engagement with the ciliary sulcus but equivalent lens can be made which are intended for capsule bag placement as shown in FIG. 4b.

Figure 5:
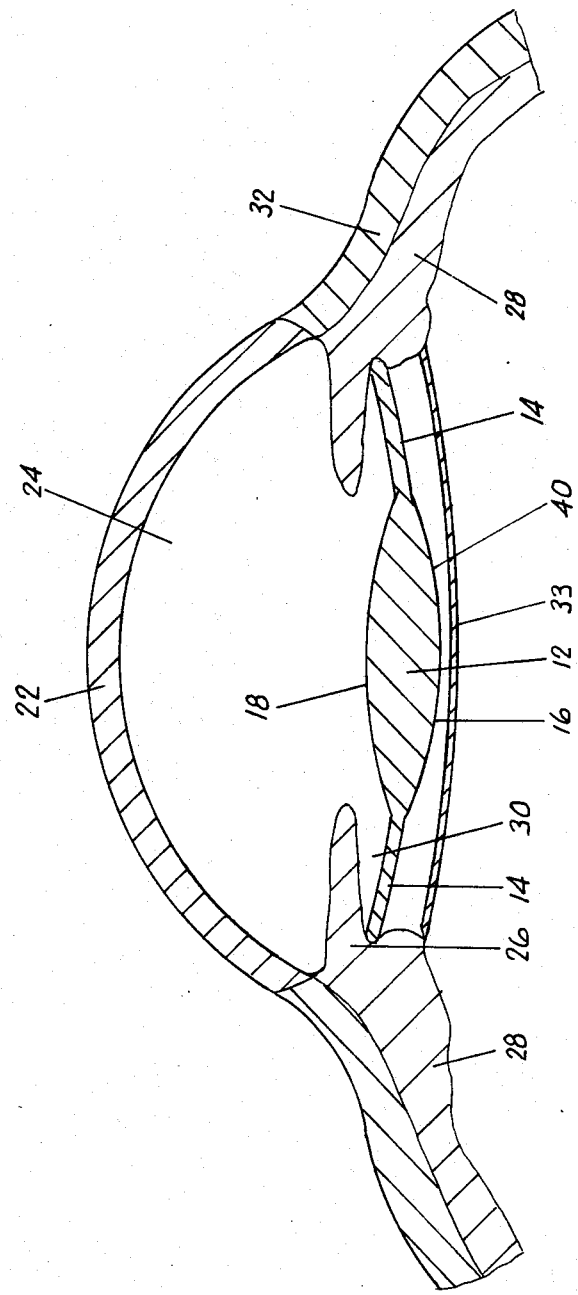
FIGS. 5 to 8, 10 and 11 are views similar to that of FIG. 4a showing alternative intraocular lens configurations in accordance with the present invention.
Figure 6:
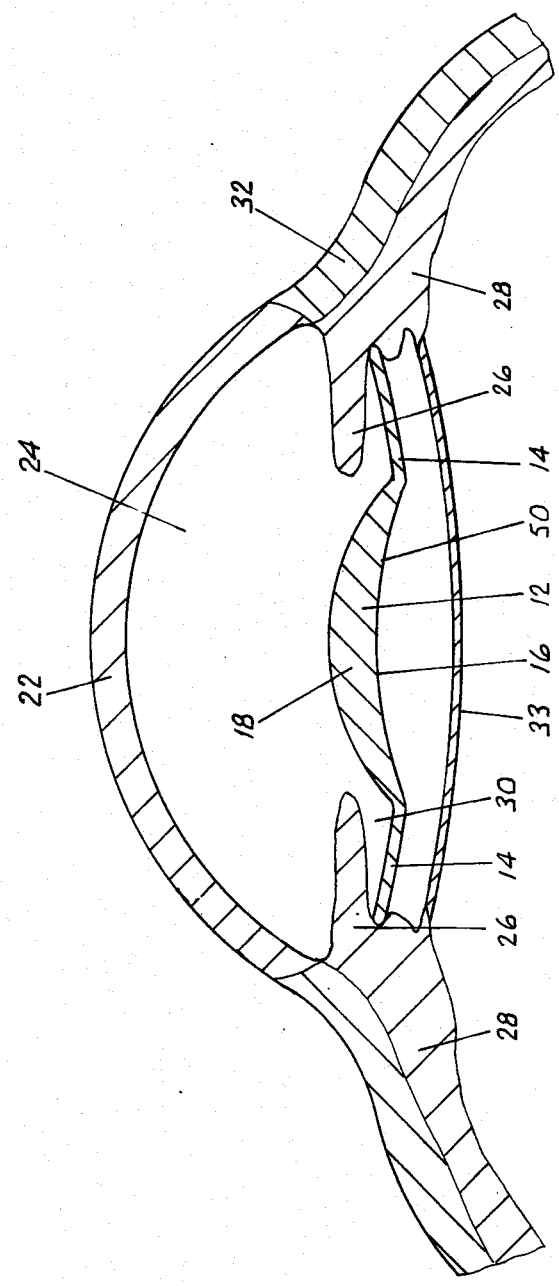

An alternative form of intraocular lens implant 40 according to the present invention intended for implantation in the posterior chamber of the eye is shown in FIG. 5. In this case, the posterior face 16 is not of uniform curvature throughout but has increased curvature in the optical portion 12. The lens 40 is still of asymmetrical biconvex construction. An alternative form of intraocular lens implant 50 according to the present invention intended for implantation in the posterior chamber of the eye is shown in FIG. 6. In this case, the posterior face 16 has reverse curvature in the optical portion 12 and the lens 50 is of convex-concave construction.

Figure 7:
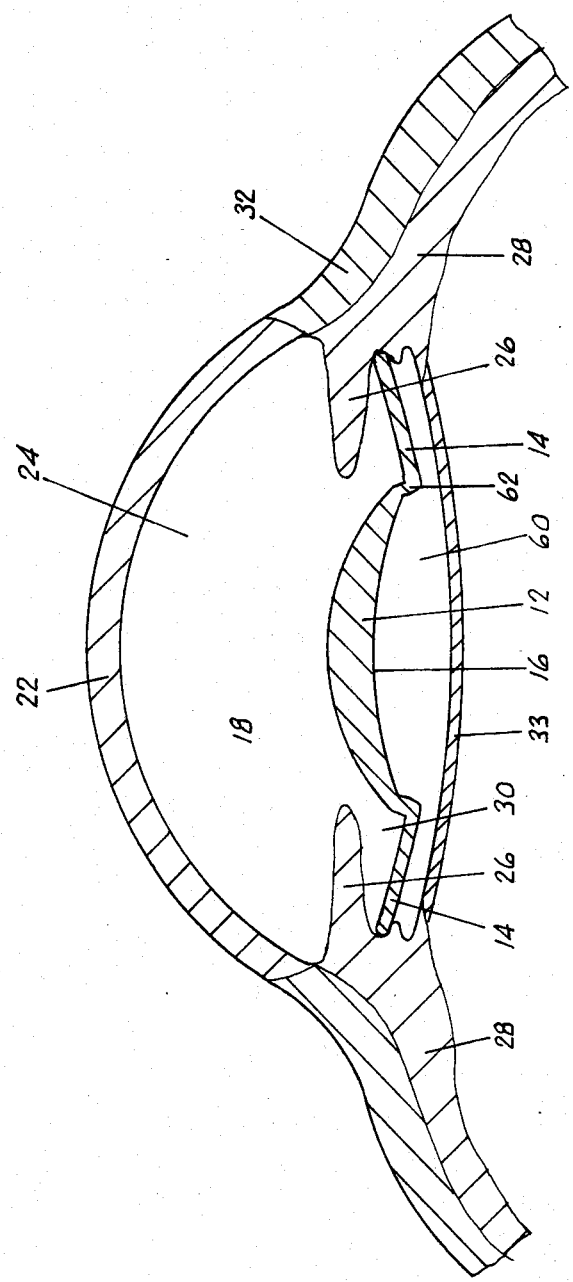

An alternative form of intraocular lens implant 60 according to the present invention intended for implantation in the posterior chamber of the eye is shown in FIG. 7. In this case, the optical portion of the posterior face 16 is located forwardly of the remainder of the posterior face 16 by means of a peripheral lip 62. The lens 60 is of asymmetrical biconvex construction.

Figure 8:
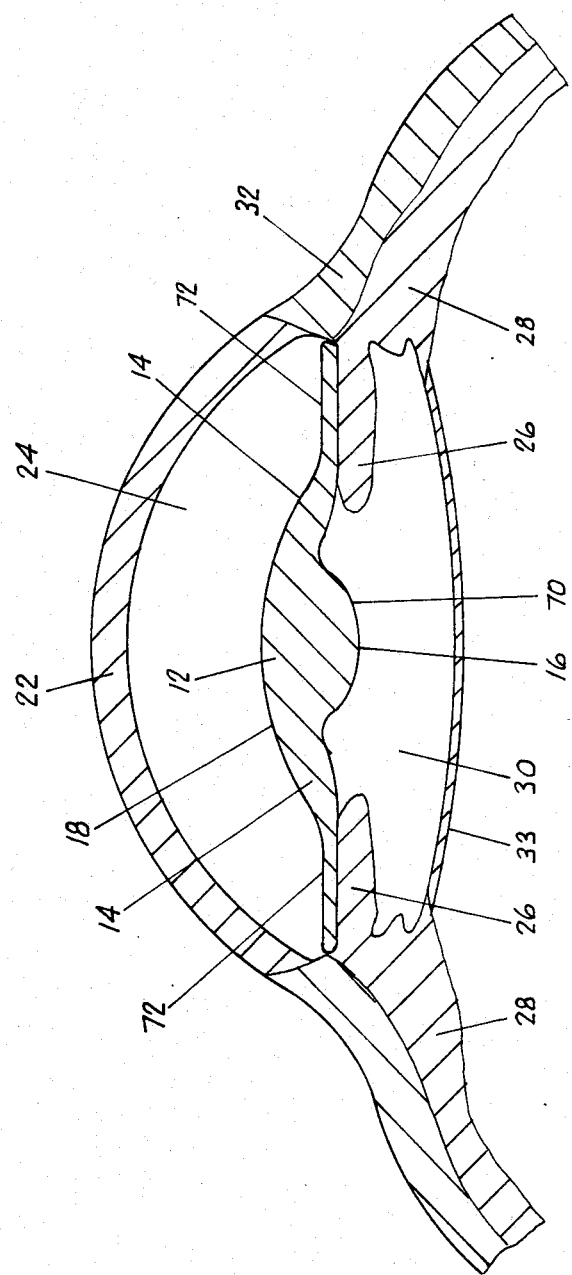
Figure 9:
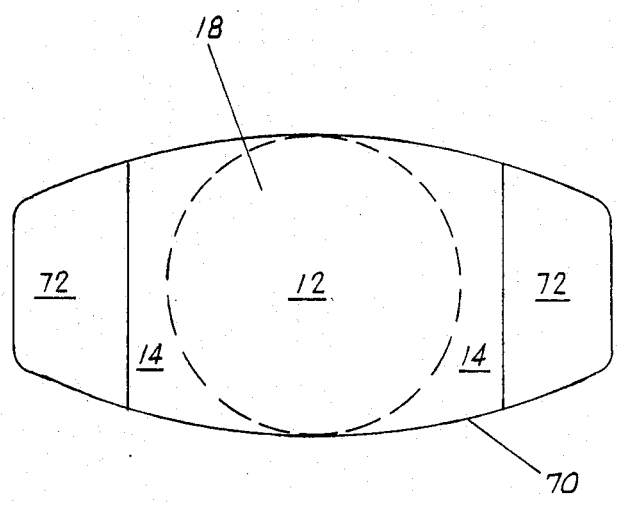
FIGS. 9 and 12 are plan views of the lens shown in FIGS. 8 and 11 respectively.

An alternative form of intraocular lens implant 70 according to the present invention intended for implantation in the anterior chamber of the eye is shown in FIGS. 8 and 9. In this case, the flanges 14 are provided with outwardly projecting feet 72 arranged to engage with the scleral spur or angle of the eye. The anterior face 18 of the implant 70 is of uniform convex curvature through the optical portion 12 and the flanges 14. The posterior face 16 also has a convex curvature so that the lens 70 is of asymmetrical biconvex construction.

Figure 10:
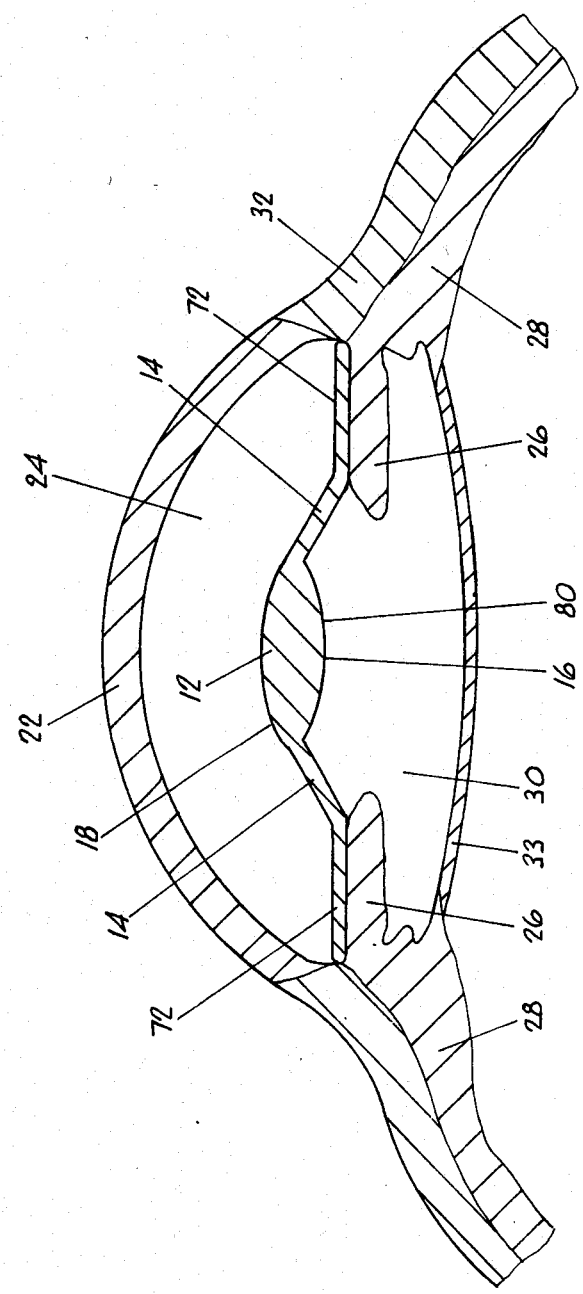

An alternative form of intraocular lens implant 80 according to the present invention intended for implantation in the anterior chamber of the eye is shown in FIG. 10. The lens of FIG. 10 is similar to that shown in FIGS. 8 and 9 and it also copmrises the outwardly projecting feet 72. However, the anterior face 18 of the lens is of increased curvature in the optical portion 12 compared to the remainder of the anterior face 18.

Figure 11:
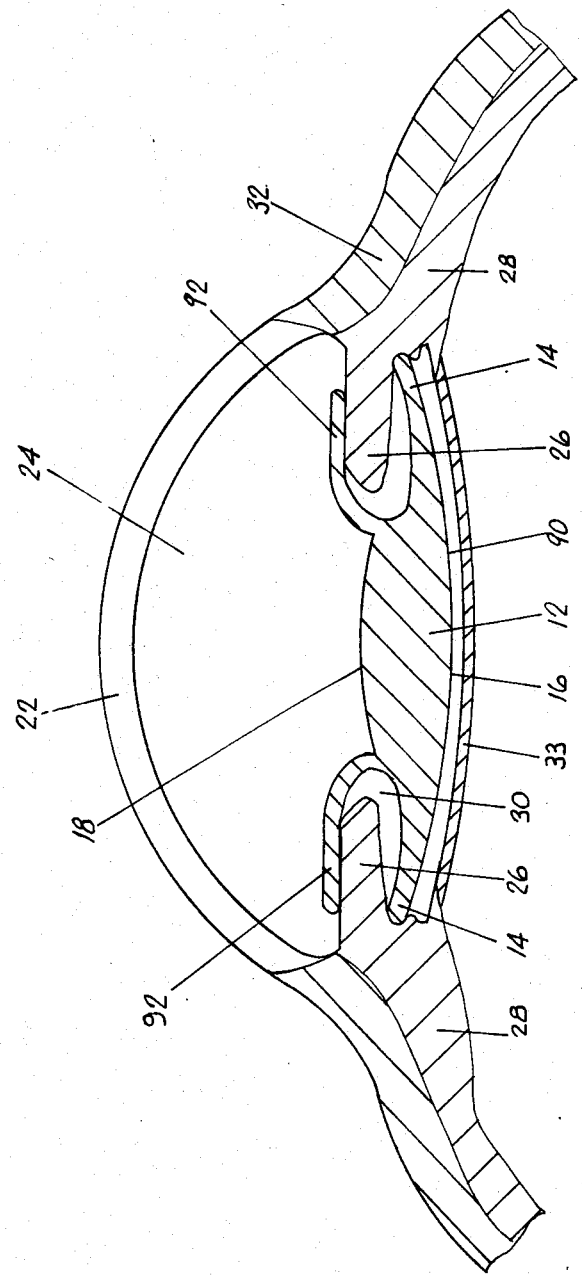
Figure 12:
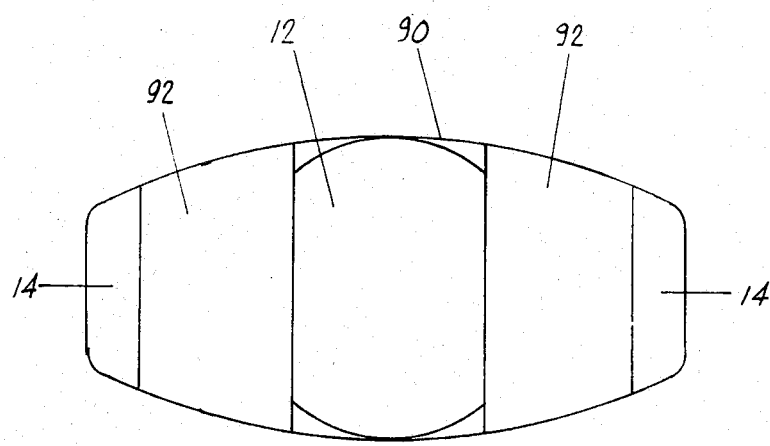
Figure 13:
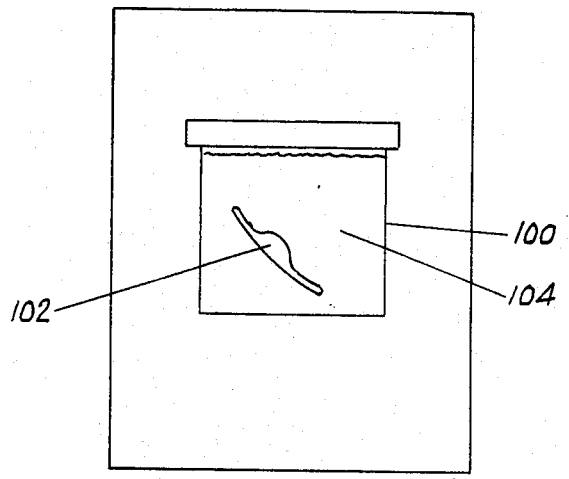
FIG. 13 is a side elevation of a package containing an intraocular lens implant in accordance with the present invention.

An alternative form of intraocular lens implant 90 according to the present invention intended for implantation in the posterior chamber of the eye is shown in FIGS. 11 and 12. The lens of FIGS. 11 and 12 comprise a pair of lugs 92 which extend upwardly and then outwardly from the anterior face 18. As shown in FIG. 11, the lugs 92 are each intended to engage with iris 26 of an eye. Thus the lugs 92 hold the lens implant 90 in place by engagement with the iris 26 but not necessarily by engagement with the ciliary sulcus 28. In other respects the lens implant 90 is similar to the lens implant shown in FIG. 4. Preferably, a manufactured lens is washed a number of times in double distilled water to remove impurities from it and then autoclaved as described above. The autoclaving may be conducted for 15 to 30 minutes at a pressure in the range from about 120 to 130 mm mercury in a sealed vial containing a physiologically acceptable electrolyte solution. Then the sterilised vial is placed inside an internally sterile overpouch which is sealed and the autoclaving process is then repeated to ensure complete sterility of the completed product. A typical package comprising a sealed vial 100 containing a lens implant 102 and a quantity of physiologically acceptable saline solution 104 all contained within a flexible overpouch 106 is shown in FIG. 13.

The diameter of the optical portion 12 of a lens implant in accordance with the present invention is preferably from 3 to 10 mm, more preferably from 4 to 7 mm. The overall length of the lens implant may be from 8 to 15 mm.

The non-variable optical surface of the optical portion 12 preferably ranges from plano to 10 mm in radius of curvature, preferably from 15 to 30 mm radius of curvature. As stated above the radius of curvature of the optical surface of varying power is varied to adjust the optical power of the lens implant.

The lens implant of the present invention is particularly envisaged for use where a cataract has been removed. However, the lens implant of the present invention may be used to correct refractive errors and myopia without prior cataract extraction.

Thus, the lens implants of the present invention usually range from plano-convex to biconvex but as shown in FIG. 6, the posterior and anterior face of the optical portion 12 may have curves facing in the same direction which results in a concave-convex lens.

The lens implant of the present invention may include location members such as indentations, recesses or holes to assist in positioning the lens in the middle of the eye. The lens implant can be inserted at the time of cataract extraction or as a secondary implant. The lens can be inserted by the standard procedure. The design of the lens also allows the flanges 14 to be inserted in a folded condition and then be allowed to open out through their own inherent resilience to engage with the ciliary sulcus 28. The flanges 14 avoid the use of prolene hooks or the like which have been used in the past.

Whilst it is preferred to insert the lens in hydrated condition from a vial as shown in FIG. 13, the lens implant could be inserted into the eye dry and hydrated subsequently to hydrate and swell it. The advantage of dry insertion is that it allows the lens implant to be inserted through a small wound in the eye.

The lens implant of the present invention may have a built in U.V. filter which is incorporated in the hydrogel. The U.V. filter can be incorporated in the chenical mix as polymerisation takes place or a U.V. absorbing function can be built into the polymeric chain.

It is also envisaged that in some cases anterior chamber lens would be incorporated into a posterior chamber of the eye by being reversed.

Modifications and variations such as would be apparent to a skilled addressee are deemed within the scope of the present invention.

I claim:

1. A self-supporting intraocular lens suitable for implantation in the human eye to replace the natural crystalline lens, comprising:
    an optical portion having an anterior surface and a convex posterior surface;
    flange means having an anterior surface and a posterior surface, said flange means extending laterally from said optical portion and projecting anteriorly, said flange means comprising a solid body which functions to support and retain the lens in place in the eye following implantation without fixation to the iris of the eye, wherein said lens is formed entirely of a hydrogel; and wherein the posterior surface of the flange means and the posterior surface of the optical portion define a single, continuous arc.

2. An intraocular lens according to claim 1, wherein the optical portion of said lens is of asymmetrical biconvex construction with the posterior surface having the larger radius of curvature.

3. An intraocular lens according to claim 1 wherein the hydrogel is hydroxyethyl methacrylate.

4. An intraocular lens according to claim 1 which is of integral construction.

5. An intraocular lens according to claim 1 wherein the optical portion has a diameter of from 3 to 10 mm.

6. An intraocular lens according to claim 5 which has a length of from 8 to 15 mm in a horizontal direction across the eye.

7. An intraocular lens according to claim 1, wherein the optical portion has a non-variable optical surface having a curvature from plano to 10 mm radius.

8. An intraocular lens according to claim 1 wherein the optical portion has a non-variable optical surface having a curvature from 15 to 30 mm radius.

9. An intraocular lens according to claim 1, which is in hydrated form.

10. An intraocular lens according to claim 1, which is in hydrated form and is contained in a sealed vial containing a quantity of physiologically acceptable electrolyte solution.

11. An intraocular lens implant according to claim 10, wherein the sealed vial is contained in a sealed overpouch.

12. An intraocular lens according to claim 1 wherein the ratio of curvature between the curvature of the posterior face and the curvature of the anterior face is on the order of 3:1.

13. An intraocular lens according to claim 1 wherein said flange means comprises a pair of flanges which extend laterally from the optical portion.

14. An intraocular lens according to claim 13 wherein said pair of flanges taper away from the optical portion.

15. An intraocular lens according to claim 1 wherein the lens is sized for being retained in position in the eye by engagement of the flange means in the ciliary sulcus or capsular bag of the eye.

16. An intraocular lens according to claim 1 wherein, on implantation of the lens in the eye, the single continuous arc formed by the posterior surface of the flange means and the posterior surface of the optical portion is sized for initial positioning adjacent the posterior capsule.

17. A self-supporting, intraocular lens, suitable for implantation in the posterior chamber of the human eye to replace the natural crystalline lens, comprising:
    an asymmetrical, biconvex optical portion having an anterior surface and a posterior surface, with the posterior surface having the larger radius of curvature; and
    flange means having an anterior surface and a posterior surface, said flange means comprising a pair of flanges disposed on opposite sides of the optical portion, said flanges extending laterally and projecting anteriorly from said optical portion, each of said flanges having a first end proximal to the optical portion and a second end distal to the optical portion, said first end having a width substantially equal to the diameter of the optical portion, said flange means functioning to support and retain the lens in place in the eye following implantation without fixation to the iris of the eye;
    wherein said lens is formed entirely of a hydrogel, and the posterior surfaces of the flange means and posterior surface of the optical portion define a single, continuous arc.

* * * * *